United States Patent
Tian et al.

(10) Patent No.: US 9,744,526 B2
(45) Date of Patent: Aug. 29, 2017

(54) SAPO-34 MOLECULAR SIEVE AND METHOD FOR PREPARING THE SAME

(71) Applicant: Dalian Institute of Chemical Physics, Chinese Academy of Sciences, Dalian, Liaoning (CN)

(72) Inventors: Peng Tian, Liaoning (CN); Zhongmin Liu, Liaoning (CN); Dong Fan, Liaoning (CN); Xiong Su, Liaoning (CN); Ying Zhang, Liaoning (CN); Yue Yang, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 141 days.

(21) Appl. No.: 14/428,545

(22) PCT Filed: Sep. 26, 2012

(86) PCT No.: PCT/CN2012/082000
§ 371 (c)(1),
(2) Date: Mar. 16, 2015

(87) PCT Pub. No.: WO2014/047802
PCT Pub. Date: Apr. 3, 2014

(65) Prior Publication Data
US 2015/0231616 A1 Aug. 20, 2015

(51) Int. Cl.
*C01B 39/54* (2006.01)
*B01J 29/85* (2006.01)
*B01J 37/08* (2006.01)
*B01J 37/00* (2006.01)

(52) U.S. Cl.
CPC ............ *B01J 29/85* (2013.01); *B01J 37/009* (2013.01); *B01J 37/0018* (2013.01); *B01J 37/08* (2013.01); *C01B 39/54* (2013.01); *B01J 2231/763* (2013.01)

(58) Field of Classification Search
CPC .. C01B 39/54; B01J 29/85; B01J 37/08; B01J 37/0018; B01J 37/009; B01J 2231/763
See application file for complete search history.

(56) References Cited

U.S. PATENT DOCUMENTS

| | | | | |
|---|---|---|---|---|
| 4,440,871 A * | 4/1984 | Lok | ............ | B01J 20/18 208/114 |
| 4,898,660 A * | 2/1990 | Wilson | ............ | B01D 15/00 208/112 |
| 5,126,308 A * | 6/1992 | Barger | ............ | B01J 29/84 502/208 |
| 5,370,851 A * | 12/1994 | Wilson | ............ | B01J 29/85 423/305 |
| 6,835,363 B1 | 12/2004 | Strohmaier | | |
| 8,232,296 B2 * | 7/2012 | Briggner | ............ | C07D 401/14 514/333 |
| 2005/0249661 A1 * | 11/2005 | Higuchi | ............ | B01J 29/85 423/700 |
| 2015/0231616 A1 * | 8/2015 | Tian | ............ | B01J 29/85 423/708 |
| 2015/0232345 A1 * | 8/2015 | Fan | ............ | C01B 39/54 423/705 |

FOREIGN PATENT DOCUMENTS

| | | |
|---|---|---|
| CN | 1299776 A | 6/2001 |
| CN | 101242900 A | 8/2008 |
| CN | 101376111 A | 3/2009 |
| CN | 102530987 A | 7/2012 |
| EP | 0 043 562 B1 | 6/1984 |
| EP | 0 538 958 A1 | 4/1993 |
| WO | 2012/071889 A1 | 6/2012 |

OTHER PUBLICATIONS

Jenkins et al, "Introduction to X-ray Powder Diffractometry", Chapter 3, (1996).*
Goodman, "Challenges and Strategies for Patenting New Solid Forms", (2014).*
Search Report issued in International Application No. PCT/CN2012/082000 dated Jul. 4, 2013 (Jul. 4, 2013).
Liu, et al., "Synthesis, characterization and catalytic properties of SAPO-34 synthesized using diethylamine as a template", Microporous and Mesoporous Materials, 111 (2008) 143-149.
Liu, et al., "Synthesis of SAPO-34 templated by diethylamine: Crystallization process and Si distribution in the crystals", Microporous and Mesoporous Materials, 114, (2008) 416-423.
Akolekar, et al., "Formation of small pore SAPO-44 type molecular sieve", Colloids and Surfaces A: Physicochemical and Engineering Aspects, 146 (1999) 375-386.

(Continued)

*Primary Examiner* — David M Brunsman
(74) *Attorney, Agent, or Firm* — Nath, Goldberg & Meyer; Jerald L. Meyer; Tanya E. Harkins

(57) ABSTRACT

A SAPO-34 molecular sieve and method for preparing the same, whose chemical composition in the anhydrous state is expressed as: $mSDA \cdot (Si_xAl_yP_z)O_2$, wherein m is 0.08-0.3, x is 0.01-0.60, y is 0.2-0.60, z is 0.2-0.60, and x+y+z=1. The template agent SDA is in micropores of the molecular sieve. SDA is an organic amine with the structural formula $(CH_3)_2NRN(CH_3)_2$, wherein R is a saturated straight-chain or branched-chain alkylene group with having from 2-5 carbon atoms. There is a slight Si enrichment phenomenon on the crystal surface of the molecular sieve crystal, and the ratio of the surface Si content to the bulk Si content of the crystal ranges from 1.50-1.01. Said SAPO-34 molecular sieve, after being calcined at a temperature range from 400-700° C. in air, can be used as a gas adsorbent and catalyst for an acid-catalyzed reaction or oxygenate to olefin reaction.

15 Claims, No Drawings

(56) References Cited

OTHER PUBLICATIONS

Vomscheid, et al., "The Role of the Template in Directing the Si Distribution in SAPO Zeolites", J. Phys. Chem., 1994, 98, 9614.

Mores, et al., "Space- and Time-Resolved In-situ Spectroscopy on the Coke Formation in Molecular Sieves: Methanol-to-Olefin Conversion over H-ZSM-5 and H-SAPO-34", Chemistry—A European Journal, 2008, 14, 11320-11327.

Hereijgers, et al., "Product shape selectivity dominates the Methanol-to-Olefins (MTO) reaction over H-SAPO-34 catalysts", Journal of Catalysis 264 (2009) 77-87.

Wilson, et al., "Synthesis, characterization and structure of SAPO-56, a member of the ABC double-six-ring family of materials with stacking sequence AABBCCBB", Microporous and Mesoporous Materials 28 (1999) 125-137.

Michele Goepper, Doctoral dissertation (Universite Haute Alsace, Mulhouse, France, 1990).

Liu, Guangyu, et al., "Synthesis of SAPO-34 templated by diethylamine: Crystallization process and Si distribution in the crystals", Microporous and Mesoporous Materials, vol. 114, pp. 416-423, 2008.

Fan, Dong, et al., "A novel solvothermal approach to synthesize SAPO molecular sieves using organic amines as the solvent and template", Journal of Materials Chemistry, vol. 22, pp. 6568-6574, 2012.

* cited by examiner

SAPO-34 MOLECULAR SIEVE AND METHOD FOR PREPARING THE SAME

This is a National Phase Application filed under 35 U.S.C. 371 as a national stage of PCT/CN2012/082000, filed Sep. 26, 2012, the content of which is hereby incorporated by reference in its entirety.

TECHNICAL FIELD

The present invention concerns a silicoaluminophosphate molecular sieve with the CHA framework, and method for preparing the same, and applications of the same in acid catalyzed reaction and an oxygenate to olefins reaction.

BACKGROUND

In 1984, a series of novel silicoaluminophosphate SAPO molecular sieves were developed in the Union Carbide Corporation (UCC) (U.S. Pat. No. 4,440,871). SAPO molecular sieves are crystallized silicoaluminophosphates with three dimensional frameworks formed by $PO_2^+$, $AlO_2^-$, and $SiO_2$ tetrahedrons. Among this kind of molecular sieves, SAPO-34 with chabazite-type framework contains 8-member ring pore, wherein the orifice size is 0.38 nm×0.38 nm. SAPO-34 has attracted attention because it has shown the excellent catalytic performance in methanol to olefins (MTO) process, due to its proper acidity and pore structure.

SAPO-34 molecular sieve is generally produced by a hydrothermal synthesis process which uses water as the solvent and is conducted in a sealed autoclave. The components for the synthesis comprise an aluminum source, a silicon source, a phosphorus source, a template agent, and deionized water. The silicon source may be chosen from silica sol, active silica, and orthosilicate esters. The aluminum source may be chosen from active alumina, pseudo boehmite, or alkoxy aluminum. Preferable silicon source and aluminum source are silica sol and pseudo boehmite. Phosphorus source is generally 85% phosphoric acid. The template agent commonly used comprises tetraethyl ammonium hydroxide (TEAOH), morpholine (MOR), piperidine, isopropylamine (i-PrNH2), triethylamine (TEA), diethylamine (DEA), dipropylamine, and the like, or a mixture thereof. In the traditional hydrothermal synthesis of SAPO-34, the molar amount of the organic amine template agent used is significantly less than the molar amount of water. Water is used as the continuous phase and the main solvent, and the molar ratio of water to organic amine template agent is generally larger than 10. In our research on hydrothermal synthesis process of SAPO-34 using diethylamine as the template agent, we found that with the amount increase of the template agent gradually, both of the product yield and crystallinity decrease to some degrees, seeing Table 1 in *Microporous and Mesoporous Materials*, 2008, 114(1-3): 4163.

Concerning the synthesized SAPO molecular sieves, several researchers have reported there is a Si enrichment phenomenon on the crystal surface. The reason is that the initial reaction mixtures to produce SAPO molecular sieves are acid or nearly neutral, and with the proceeding of crystallization, the pH values of the initial reaction mixtures rise gradually because the consumption of phosphoric acid which enters into molecular sieves. In the beginning of crystallization, the silicon source exists generally in the form of polymers. Because of the low isoelectric point, the silicon source decomposes by degrees with the rise of pH value, making the proportion of silicon entering in the framework of SAPO molecular sieves increase, leading to the Si enrichment phenomenon on the crystal surface. For instance, in our research on hydrothermal synthesis process of SAPO-34 using diethylamine as the template agent, we found that a non-uniform distribution of Si in the crystal shows a gradual increase of the Si content from the core to the surface, and the ratio of the Si content (molar ratio Si/(Si+Al+P)) on the surface to the Si content in the crystal bulk is 1.41 (*Microporous and Mesoporous Materials*, 2008, 114(1-3): 4163). Akolekar et al found that in the SAPO-44 crystal, the molar ratio of the Si content (molar ratio Si/(Si+Al+P)) on the surface to the Si content in the crystal bulk is from 6 to 10 (*Colloids and Surfaces A: Physicochemical and Engineering Aspects*, 146 (1999) 375-386). In general, SAPO molecular sieves show the character of an obvious Si enrichment phenomenon on the crystal surface, but it has been noticed that, even for the same kind of SAPO molecular sieve, there are obvious difference between the elementary composition on the crystal surface and inside the crystal, which changes with the synthesis conditions and the template agents.

Usually, with the increase of Si content in SAPO molecular sieves, the Si coordination structures change from Si(4Al) to Si(nAl) (n=0 to 4) (in different kind of SAPO molecular sieves, the allowable maximum of single Si distribution in the frameworks are different, seeing *J. Phys. Chem.*, 1994, 98, 9614). The Si coordination structures have significant effect on the acid concentration and the acid intensity, and the acid intensity is enhanced in the order of Si(1Al)>Si(2Al)>Si(3Al)>Si(4Al). In the other hand, the amount of acid center produced by each Si atom decrease with the appearance of Si islands in the framework of SAPO molecular sieves (Si(4Al) is 1, and the others are less 1), leading to the decrease of the acid concentration. It is supposed that using the SAPO molecular sieves as the acid catalyst, the catalytic performance must be effected by the distribution of Si in the framework since the non-uniform distribution of Si in crystal bring the non-uniform distribution of acidity. The enrichment of Si on the surface of crystal indicates that the Si coordination structures on the surface of crystal are more complex than inside the crystal. Weckhuysen et al have reported that in the process of methanol to olefin (MTO), reaction firstly occurs near the surface of crystal, and with the reaction going on, the large coke species form and block the pores progressively, making the diffusion of the products inside the crystal more difficult (*Chemistry—A European Journal*, 2008, 14, 11320-11327; *J. Catal.*, 2009, 264, 77-87). It indicates that the acid environment on the surface of molecular sieve crystal is very important to the catalytic performance, and it is significant to seek a control method of the degree of Si enrichment on the molecular sieve surfaces.

The elementary analysis of molecular sieve surfaces generally is detected using the XPS method, and the elementary distribution form the core to shell is detected using the EDX method of SEM by line scan after cutting the crystal.

The hydrothermal synthesis of AlPO-21 molecular sieve was reported in European patent 0043562 using N,N,N',N'-tetramethyl ethylenediamine as the template agent. The synthesis of aluminum phosphate molecular sieve SCS-24 was reported in European patent 0538958 using N,N,N',N'-tetramethyl ethylenediamine as the template agent. The synthesis of AlPO-21 molecular sieve was reported in U.S. Pat. No. 4,898,660 using N,N,N',N'-tetramethyl-1,3-diaminopropane and N,N,N',N'-tetramethyl ethylenediamine as the template agents. The synthesis of SAPO-56 was reported in U.S. Pat. No. 5,370,851 using N,N,N',N'-tetramethyl-1,6-hexanediamine as the template agent. Wilson et al reported the synthesis of AlPO-17, SAPO-17, and SAPO-56 using N,N,N',N'-tetramethyl-1,6-hexanediamine as the template agent (Mico. Meso. Mater. 1999, 28(1), 117-126). M. Goepper from France reported the synthesis of AlPO-34 in his doctoral dissertation (Universite Haute Alsace, Mulhouse, France, 1990), using N,N,N',N'-tetramethyl ethylenediamine (TMED) as the template agent, under the existence of hydrogen fluoride (with the mixture ratio of 1.0HF: 1.5TMED:1$Al_2O_3$:1$P_2O_5$:80$H_2O$, crystallized at 200° C. for 24 h). According to the above doctoral dissertation, the product with CHA framework could not be obtained as adding the divalent metal ions in the synthesis system, and when there was no fluorion in the synthesis system, the product obtained was AlPO-21. The hydrothermal synthesis of AlPO-34 and SAPO-34 with low content of silicon was reported in U.S. Pat. No. 6,835,363 using the organic amines with two dimethylamino—as the template agents, under the existence of hydrogen fluoride.

Accordance to the above report, in research of synthesis of the molecular sieves using the organic amines with two dimethylamino—as the template agents, AlPO-34 and SAPO-34 could be obtained under proper synthesis condition and existence of fluorion. When there was no fluorion in the hydrothermal synthesis system, the products obtained were the molecular sieves with other frameworks. It indicates that the fluorion plays important role in the hydrothermal synthesis of the molecular sieves with CHA framework.

It is well known that the fluorion has strong corrosiveness to steel. In the large-scale produce of AlPO-34 and SAPO-34 molecular sieves, the corrosion of steel autoclave by the fluorion in the synthesis system is a problem which cannot be ignored. It has an important scientific value and utility value to seek a fast and efficient synthesis method of SAPO-34 without use of fluorion-containing system.

DISCLOSURE

An object of the present invention is to provide a SAPO-34 molecular sieve, whose chemical composition in the anhydrous state is expressed as: $mSDA \cdot (Si_xAl_yP_z)O_2$; wherein, SDA represents the template agent existing in micropore of said molecular sieve; m is the molar number of said template agent per one mole of $(Si_xAl_yP_z)O_2$, and m is from 0.08 to 0.3; x, y, z respectively represents the molar number of Si, Al, P, and x is from 0.01 to 0.60, and y is from 0.2 to 0.60, and z is from 0.2 to 0.60, and x+y+z=1. SDA is organic amine with the structural formula as $(CH_3)_2NRN(CH_3)_2$, wherein R is saturated straight-chain or branch-chain alkylene group with the number of carbon atoms at a range from 2 to 5. Said template agent SDA is one or more selected from N,N,N',N'-tetramethyl ethylenediamine, N,N,N',N'-tetramethyl-1,3-diaminopropane, N,N,N',N'-tetramethyl-1,4-butanediamine, N,N,N',N'-tetramethyl-1,5-pentane diamine, N,N,N',N'-tetramethyl-1,2-diaminopropane, N,N,N',N'-tetramethyl-1,3-butanediamine, N,N,N',N'-tetramethyl-1,4-pentane diamine. There is a slight Si enrichment phenomenon on the crystal surface of said molecular sieve crystal, and the ratio of the surface Si content to the bulk Si content of the crystal (the Si content is calculated by the molar ratio of Si/(Si+Al+P)) ranges from 1.50 to 1.01, preferably ranges from 1.42 to 1.02, further preferably ranges from 1.35 to 1.03, and more further preferably ranges from 1.30 to 1.03. The Si contents from core to shell of said molecular sieve crystals increase uniformly or non-uniformly.

Another object of the present invention is to provide a method for preparing SAPO-34 molecular sieve. Another object of the present invention is to provide a SAPO-34 molecular sieve prepared using the above method and catalysts prepared from the same for acid-catalyzed reaction or an oxygenate to olefins reaction.

Another object of the present invention is to provide a SAPO-34 molecular sieve prepared using the above method and a gas adsorbent prepared from the same.

The technical problem to be solved in the present invention is that the SAPO-34 molecular sieve is fast prepared in high yield without use of fluorion, using the organic amine with the structural formula as $(CH_3)_2NRN(CH_3)_2$ as the template agent. The inventers of the present invention found by experimental research that the SAPO-34 molecular sieve can be fast prepared by using the organic amine with the structural formula as $(CH_3)_2NRN(CH_3)_2$ as the template agent and main solvent, controlling the molar ratio of $(CH_3)_2NRN(CH_3)_2/H_2O$ and using the proper order of ingredients addation. Comparing with the SAPO-34 molecular sieve prepared by the hydrothermal method using the same template agent in fluorion-containing system, the yield of the SAPO-34 molecular sieve prepared by said method in present invention is obviously improved. It is more important that there is a slight Si enrichment phenomenon on the surface of the product crystals prepared by the method in the present invention. This phenomenon might have relationship with the strong basicity environment in the synthesis system. The pH values alteration is not obviously at the crystallization process of initial period to the final period, and in the initial of crystallization, the silicon source exists in low degree of polymerization, making the proportion of silicon taking part in the formation of the molecular sieve crystal higher than using traditional methods, leading to a significant decrease of the Si enrichment degree on the molecular sieve surfaces.

The present invention refers to a method for preparing SAPO-34 molecular sieve, including the steps as follows:
(a) a silicon source, an aluminum source, a phosphorus source, deionized water and SDA are mixed, and an initial gel mixture with following molar ratio is obtained:
$SiO_2/Al_2O_3$ is from 0.01 to 1;
$P_2O_5/Al_2O_3$ is from 0.5 to 1.5;
$H_2O/Al_2O_3$ is from 1 to 19;
$SDA/Al_2O_3$ is from 5 to 30;
$SDA/H_2O$ is from 0.27 to 30;
wherein, SDA is organic amine with the structural formula as $(CH_3)_2NRN(CH_3)_2$, wherein R is saturated straight-chain or branch-chain alkylene group with the number of carbon atoms at a range from 2 to 5;
(b) the initial gel mixture obtained in said step (a) is transferred into a synthetic kettle, then sealed and heated to crystallization temperature range from 170° C. to 220° C., crystallized for crystallization time range from 0.5 h to 48 h under the autogenous pressure;
(c) after finishing the crystallization, the solid product is centrifugal separated, washed to neutral using deionized water and dried to obtain said SAPO-34 molecular sieve.

In the initial gel mixture obtained in said step (a), the silicon source is one or more selected from silica sol, active silica, orthosilicate esters and metakaolin; the aluminum source is one or more selected from aluminum salts, activated alumina, aluminum alkoxide and metakaolin; the phosphorus source is one or more selected from phosphoric acid, diammonium hydrogen phosphate, ammonium dihydrogen phosphate, organophosphorous compounds and phosphorus oxides.

In the initial gel mixture obtained in said step (a), the molar ratio of organic amine SDA to water SDA/H$_2$O is from 0.5 to 30, and preferably the molar ratio of SDA to water SDA/H$_2$O is from 1.0 to 30.

In the initial gel mixture obtained in said step (a), the molar ratio of organic amine SDA to Al$_2$O$_3$ SDA/Al$_2$O$_3$ is from 7.0 to 30.

The organic amine SDA in said step (a) is selected from N,N,N',N'-tetramethyl ethylenediamine, N,N,N',N'-tetramethyl-1,3-diaminopropane, N,N,N',N'-tetramethyl-1,4-butanediamine, N,N,N',N'-tetramethyl-1,5-pentane diamine, N,N,N',N'-tetramethyl-1,2-diaminopropane, N,N,N',N'-tetramethyl-1,3-butanediamine, N,N,N',N'-tetramethyl-1,4-pentane diamine.

In said step (a), the order of ingredients addation is as follows: firstly, mixing homogeneously the aluminum source and the organic amine SDA by stirring to obtain the mixture A; after continuously stirring the mixture of the silicon source, the phosphorus source and deionized water, mixing homogeneously the mixture A and the mixture of the silicon source, the phosphorus source and deionized water by stirring to obtain the initial gel mixture.

In said step (b), the crystallization condition are the crystallization temperature range from 180° C. to 210° C. and the crystallization time range from 1 h to 24 h; and preferably the crystallization condition are the crystallization temperature range from 190° C. to 210° C. and the crystallization time range from 1 h to 12 h.

In said step (b), the crystallization is carried out dynamically.

The yield of SAPO-34 product is greater than 85%. The calculation method of product yield is: the mass of solid product after calcined at 600° C. to remove the template agent×100%/the total mass of inorganic oxides in the initial gel mixture.

The present invention also refers to a catalyst for acid-catalyzed reaction, which is obtained by calcining at least one of said SAPO-34 molecular sieves or at least one of the SAPO-34 molecular sieves prepared by said methods, at a temperature from 400 to 700° C. in air.

The present invention also refers to a catalyst for an oxygenate to olefins reaction, which is obtained by calcining at least one of said SAPO-34 molecular sieves or at least one of the SAPO-34 molecular sieves prepared by said methods, at a temperature from 400 to 700° C. in air.

The present invention can bring the advantages including:
(1) obtaining a SAPO-34 molecular sieve using organic amine (CH$_3$)$_2$NRN(CH$_3$)$_2$ as the template agent, characterized in a slight Si enrichment phenomenon on the crystal and with the ratio of the surface Si content to the bulk Si content of the crystal (the Si content is calculated by the molar ratio of Si/(Si+Al+P)) ranging from 1.50 to 1.01.
(2) obtaining a SAPO-34 molecular sieve using organic amine (CH$_3$)$_2$NRN(CH$_3$)$_2$ as the organic solvent and the template agent simultaneously, without use of toxic and corrosive fluorion which is liable to cause environmental.
(3) comparing with the SAPO-34 molecular sieve prepared by the hydrothermal method using organic amine (CH$_3$)$_2$NRN(CH$_3$)$_2$ template agent in fluorion-containing system, the yield of the SAPO-34 molecular sieve prepared by said method in present invention is obviously improved (calculation method: the mass of solid product after calcined/the total mass of inorganic oxides in the initial gel mixture×100%).
(4) less usage of water in the synthesis system which is environment-friendly and benefit to separate and recycle of organic amine, and reduce the production of waste water.
(5) the SAPO-34 molecular prepared by said method in present invention having excellent catalytic performance and gas adsorption performance.

SPECIFIC EMBODIMENTS OF THE INVENTION

The elemental analysis of the bulk composition was determined with X-ray Fluorescence (XRF) at PANalytical X'Pert PRO X-ray diffractometer with Cu target (λ=0.15418 nm), operated at 40 KV and 100 mA.

The elemental analysis of the surface composition was determined with XPS at Thermo ESCALAB 250Xi X-Ray Photoelectron Spectrometer (Mono AlKα X-ray source) using Al2p=74.7 eV of Al$_2$O$_3$ in sample surface as internal standard to calibrate charge of sample surface.

The present invention will be described in details by Examples, but the present invention is not limited to these Examples.

EXAMPLES 1 TO 18

The amount of ingredients and the crystallization condition are shown in Table 1. The synthesis process was as follows: the aluminum sources were mixed with the organic amines (with purity of 99.5 wt %), mixing homogeneously by stirring to obtain the mixture A. The silicon sources were mixed with the phosphorus sources and deionized water and the mixtures were stirred for 30 min and added into the mixture A, then under sealed condition vigorously stirred for 30 min to obtain initial gel mixtures. The initial gel mixtures were transferred into the stainless steel synthetic kettle, then sealed and heated to crystallization temperature, crystallized dynamically for crystallization time. After finishing the crystallization, the solid product was centrifugal separated, washed, and dried at 100° C. in air to obtain raw powder samples. The samples prepared were detected by XRD, indicating that the sample prepared was SAPO-34 molecular sieve. XRD data of the sample obtained in Example 1 were shown in Table 2. XRD results of the samples obtained in Examples 2 to 18 were similar to the sample obtained in Example 1, which showed that each corresponding peak had the same peak position and the ±10% difference of peak intensity, indicating that all the samples prepared in Examples 2 to 18 were SAPO-34 molecular sieve. The inorganic elemental analysis of the surface composition and the bulk composition of the samples were detected with XPS and XRF, respectively, and results were shown in Table 1. The organic content of the samples were detected with CHN analyzer. The chemical compositions of the raw powders of molecular sieves were obtained by normalization of CHN and XRF results, which were shown in Table 1.

TABLE 1

The list of amount of ingredients and crystallization conditions of the molecular sieves*

| Example | organic amine | Aluminum source | Phosphorus source | Silicon source | H₂O | Crystallization Temperature | Crystallization Time | Product Yield [a] | A [f] | Chemical Composition [g] |
|---|---|---|---|---|---|---|---|---|---|---|
| 1 | N,N,N',N'-tetramethyl ethylenediamine 60 g | 10 g | 14.7 g | 4.3 g | 1.0 g | 190° C. | 12 h | 90.4% | 1.37 | $0.15R \cdot (Al_{0.49}P_{0.40}Si_{0.11})O_2$ |
| 2 | N,N,N',N'-tetramethyl-1,3-diaminopropane 65.3 g | 10 g | 14.7 g | 4.3 g | 1.0 g | 190° C. | 12 h | 88.2% | 1.30 | $0.13R \cdot (Al_{0.50}P_{0.40}Si_{0.10})O_2$ |
| 3 | N,N,N',N'-tetramethyl-1,4-butanediamine 72 g | 10 g | 14.7 g | 2.2 g | 1.0 g | 180° C. | 12 h | 87.6% | 1.35 | $0.11R \cdot (Al_{0.52}P_{0.42}Si_{0.06})O_2$ |
| 4 | N,N,N',N'-tetramethyl-1,5-pentane diamine 79 g | 10 g | 14.7 g | 4.3 g | 1.0 g | 190° C. | 12 h | 88.9% | 1.21 | $0.08R \cdot (Al_{0.50}P_{0.41}Si_{0.09})O_2$ |
| 5 | N,N,N',N'-tetramethyl-1,2-diaminopropane 65.3 g | 10 g | 14.7 g | 4.3 g | 1.0 g | 210° C. | 12 h | 91.5% | 1.02 | $0.13R \cdot (Al_{0.50}P_{0.40}Si_{0.10})O_2$ |
| 6 | N,N,N',N'-tetramethyl-1,3-butanediamine 72 g | 10 g | 14.7 g | 2.2 g | 1.0 g | 190° C. | 12 h | 88.9% | 1.23 | $0.10R \cdot (Al_{0.53}P_{0.42}Si_{0.05})O_2$ |
| 7 | N,N,N',N'-tetramethyl-1,4-pentane diamine 79 g | 10 g | 14.7 g | 4.3 g | 1.0 g | 190° C. | 1 h | 85.2% | 1.30 | $0.10R \cdot (Al_{0.50}P_{0.42}Si_{0.08})O_2$ |
| 8 | N,N,N',N'-tetramethyl ethylenediamine 60 g | 7.8 g [c] | 14.7 g | 4.3 g [b] | 0 g | 210° C. | 24 h | 92.1% | 1.35 | $0.17R \cdot (Al_{0.50}P_{0.40}Si_{0.10})O_2$ |
| 9 | N,N,N',N'-tetramethyl ethylenediamine 60 g | 7.8 g [c] | 11.5 g | 2.8 g [d] | 0 g | 190° C. | 12 h | 90.0% | 1.30 | $0.14R \cdot (Al_{0.48}P_{0.39}Si_{0.13})O_2$ |
| 10 | N,N,N',N'-tetramethyl ethylenediamine 60 g | 20 g [e] | 14.7 g | 4.3 g | 0 g | 190° C. | 12 h | 89.3% | 1.20 | $0.13R \cdot (Al_{0.50}P_{0.40}Si_{0.10})O_2$ |
| 11 | N,N,N',N'-tetramethyl ethylenediamine 120 g | 7.8 g [c] | 14.7 g | 4.3 g [b] | 0 g | 190° C. | 12 h | 90.3% | 1.25 | $0.14R \cdot (Al_{0.50}P_{0.41}Si_{0.09})O_2$ |
| 12 | N,N,N',N'-tetramethyl ethylenediamine 120 g | 7.8 g [c] | 14.7 g | 4.3 g [b] | 0 g | 210° C. | 6 h | 91.0% | 1.01 | $0.14R \cdot (Al_{0.50}P_{0.41}Si_{0.09})O_2$ |
| 13 | N,N,N',N'-tetramethyl ethylenediamine 60 g | 7.8 g [c] | 14.7 g | 4.3 g [b] | 0 g | 170° C. | 48 h | 87.6% | 1.39 | $0.13R \cdot (Al_{0.50}P_{0.41}Si_{0.09})O_2$ |
| 14 | N,N,N',N'-tetramethyl-1,3-diaminopropane 58 g | 2.5 g | 3.6 g | 1.1 g | 0 g | 220° C. | 0.5 h | 85.3% | 1.40 | $0.11R \cdot (Al_{0.50}P_{0.42}Si_{0.08})O_2$ |
| 15 | N,N,N',N'-tetramethyl-1,4-butanediamine 92 g | 7.8 g [c] | 14.7 g | 4.3 g [b] | 0 g | 180° C. | 24 h | 86.8% | 1.30 | $0.10R \cdot (Al_{0.50}P_{0.41}Si_{0.09})O_2$ |
| 16 | N,N,N',N'-tetramethyl-1,2-diaminopropane 84 g | 7.8 g [c] | 19.6 g | 4.3 g [d] | 0 g | 185° C. | 20 h | 88.2% | 1.10 | $0.11R \cdot (Al_{0.42}P_{0.31}Si_{0.27})O_2$ |
| 17 | N,N,N',N'-tetramethyl ethylenediamine 60 g | 10 g | 16.4 g | 4.3 g | 5.3 g | 210° C. | 10 h | 86.1% | 1.35 | $0.14R \cdot (Al_{0.50}P_{0.43}Si_{0.07})O_2$ |
| 18 | N,N,N',N'-tetramethyl ethylenediamine 60 g | 10 g | 16.4 g | 2.2 g | 1.0 g | 190° C. | 12 h | 89.2% | 1.25 | $0.14R \cdot (Al_{0.50}P_{0.44}Si_{0.06})O_2$ |

*All of the organic amines were analytically pure (with the mass percent of 99.5%); the aluminum source was pseudoboehmite (with $Al_2O_3$ mass percent of 72.5%); the phosphorus source was phosphoric acid (with $H_3PO_4$ mass percent of 85%); the silicon source was silica sol (with $SiO_2$ mass percent of 30%).
[a] Product yield = the mass of solid product (after calcined at 600° C. to remove the template agent) × 100%/the total mass of inorganic oxides in the initial gel mixture.
[b] the silicon source was tetraethoxysilane.
[c] the aluminum source was γ-alumina with $Al_2O_3$ mass percent of 93%.
[d] the silicon source was fumed silica (with $SiO_2$ mass percent of 93%).
[e] the aluminum source was aluminium isopropoxide.
[f] A = $Si_{surface}/Si_{bulk}$, wherein $Si_{surface}$ is the surface Si content calculated by the molar ratio of Si/(Si + Al + P) according to the result of XPS; $Si_{bulk}$ is the bulk Si content calculated by the bulk molar ratio of Si/(Si + Al + P) according to the result of XRF.
[g] R represented the organic amines.

TABLE 2

XRD result of the sample obtained in Example 1

| No. | 2θ | d(Å) | 100 × I/I₀ |
|---|---|---|---|
| 1 | 9.4545 | 9.35457 | 95.82 |
| 2 | 12.8344 | 6.8977 | 18.65 |
| 3 | 13.9189 | 6.3626 | 15.31 |
| 4 | 15.9622 | 5.55246 | 46.38 |
| 5 | 17.6853 | 5.01515 | 28.06 |
| 6 | 18.5142 | 4.79245 | 4.10 |
| 7 | 18.9682 | 4.67876 | 9.28 |
| 8 | 20.5336 | 4.32546 | 100 |
| 9 | 21.9097 | 4.05682 | 4.38 |
| 10 | 22.3181 | 3.98348 | 1.91 |
| 11 | 22.9725 | 3.87147 | 3.98 |
| 12 | 24.0990 | 3.69299 | 31.06 |
| 13 | 24.8162 | 3.58786 | 43.74 |
| 14 | 25.8284 | 3.44951 | 14.2 |
| 15 | 27.5669 | 3.23579 | 6.67 |
| 16 | 28.0275 | 3.18365 | 5.6 |
| 17 | 29.4615 | 3.03188 | 3.28 |
| 18 | 30.5062 | 2.92796 | 28.80 |
| 20 | 30.9433 | 2.88759 | 14.27 |
| 21 | 31.4801 | 2.83956 | 18.49 |
| 22 | 32.2688 | 2.77194 | 1.71 |
| 23 | 33.3591 | 2.68379 | 2.51 |
| 24 | 34.4001 | 2.60492 | 6.21 |
| 25 | 34.8399 | 2.57304 | 1.75 |
| 26 | 35.8666 | 2.50171 | 3.61 |
| 27 | 38.3234 | 2.34679 | 1.02 |
| 28 | 39.5752 | 2.27539 | 2.70 |
| 29 | 42.6257 | 2.11935 | 3.96 |
| 30 | 43.2903 | 2.08834 | 2.09 |
| 31 | 47.5413 | 1.91105 | 4.00 |
| 32 | 48.6651 | 1.86951 | 3.80 |
| 33 | 49.0438 | 1.85596 | 3.21 |

EXAMPLE 19

The synthesis process, the amount of ingredients and the crystallization condition were the same as Example 1, except that the organic amine template was changed to 30 g of N,N,N',N'-tetramethyl ethylenediamine and 30 g of N,N,N',N'-tetramethyl-1,3-diaminopropan. After the crystallization, the solid product was centrifuged for separation, washed and dried at 100° C. in air. 19.4 g of the raw powder sample was obtained (with mass loss of 15% after calcined at 600° C.) and the product yield was 88.5%. The sample was detected with XRD. XRD data of sample were similar to the sample obtained in Example 1, which showed that each corresponding peak had the same peak position and the ±10% difference of peak intensity, indicating the sample prepared was SAPO-34 molecular sieve. The elemental analysis of the surface composition and the bulk composition of the sample were detected with XPS and XRF, showing the ratio of $Si_{surface}/Si_{bulk}$ was 1.25.

EXAMPLE 20

The synthesis process, the amount of ingredients and the crystallization condition were the same as Example 1, except that the organic amine template agent was changed to 40 g of N,N,N',N'-tetramethyl-1,3-diaminopropan and 20 g of N,N,N',N'-tetramethyl-1,2-diaminopropan. After the crystallization, the solid product was centrifuged for separation, washed and dried at 100° C. in air. 20.1 g of the raw powder sample was obtained (with mass loss of 16.5% after calcined at 600° C.) and the product yield was 90.1%. The sample was detected with XRD. XRD data of sample were similar to the sample obtained in Example 1, which showed that each corresponding peak had the same peak position and the ±10% difference of peak intensity, indicating the sample prepared was SAPO-34 molecular sieve. The elemental analysis of the surface composition and the bulk composition of the sample were detected with XPS and XRF, showing the ratio of $Si_{surface}/Si_{bulk}$ was 1.15.

EXAMPLE 21

3 g of the samples obtained in Examples 1 to 3 respectively, were put into plastic beakers, adding 3 ml of 40% hydrofluoric acid to dissolve the framework of molecular sieve, and then adding 15 ml of tetrachloromethane to dissolve the organic compounds. The organic compounds were analyzed with GC-MS. The results indicated that the organic compounds in the samples obtained in Examples 1 to 3 were N,N,N',N'-tetramethyl ethylenediamine, N,N,N',N'-tetramethyl-1,3-diaminopropan, and N,N,N',N'-tetramethyl butanediamine, respectively.

EXAMPLE 22

The sample obtained in Example 1 (with the rhombohedral morphology and the crystal size from 1 μm to 5 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.18 and the atomic ratio of Si/Al near the surface area of the crystal was about 0.28.

The sample obtained in Example 2 (with the rhombohedral morphology and the crystal size from 1 μm to 5 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.17 and the atomic ratio of Si/Al near the surface area of the crystal was about 0.25.

The sample obtained in Example 3 (with the rhombohedral morphology and the crystal size from 1 μm to 5 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.10 and the atomic ratio of Si/Al near the surface area of the crystal was about 0.16.

The sample obtained in Example 18 (with the rhombohedral morphology and the crystal size from 1 μm to 5 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.09 and the atomic ratio of Si/Al near the surface area of the crystal was about 0.14.

EXAMPLE 23

Recycle of Organic Amine Solution

The synthesis process, the amount of ingredients and the crystallization condition were the same as Example 1. The stainless steel synthetic kettle was kept at 190° C. for 12 h, taken out from the oven and cooled rapidly with water. Then, the stainless steel synthetic kettle was open, from which the organic amine was separated in fume cupboard (Due to the low water amount in the synthesis system, after finishing the crystallization, under quiescent condition the synthesis system automatically separated into two phases which were the organic amine phase in upper layer and the gel-like substance phase with low fluidity in under layer. 57.6 g of the organic amine solution was collected and analyzed with gas chromatography and combination of gas chromatography and mass spectrometry (capillary column SE-30). The result indicated there were 1.5 g of water and 56.1 g of N,N,N',N'-tetramethyl ethylenediamine.

The organic amine solution collected was recycled in the preparation of molecular sieve (adding a few fresh N,N,N',N'-tetramethyl ethylenediamine), and the synthesis process, the amount of ingredients and the crystallization condition were the same as Example 1. After the crystallization, the solid product was centrifuged for separation, washed and dried at 100° C. in air. 20.3 g of the raw powder sample was obtained (with mass loss of 16.1% after calcined at 600° C.) and the product yield was 91.4%. The sample was detected with XRD, indicating that the sample prepared was SAPO-34 molecular sieve. XRD data of the sample were similar to Table 2, which showed that each corresponding peak had the same peak position and peak shape, and the intensity of the strongest peak was about 105% of the sample obtained in Example 1.

COMPARATIVE EXAMPLE 1

16.4 g of phosphoric acid (85 wt %), 17.6 g of water and 10 g of pseudo-boehmite (72.5 wt %) were added into the synthetic kettle in sequence, stirred for 30 min to obtain a homogeneous mixture. 8.3 g of N,N,N',N'-tetramethyl ethylenediamine, 2.3 g of tetraethoxysilane, 1.4 g of HF solution (50%) and 11.2 g of deionized water were homogeneously mixed by stirring, and added to the homogeneous mixture obtained above. After stirring for 2 h under sealed condition, an initial gel mixture was obtained. The initial gel mixture was transferred into the stainless steel synthetic kettle, then heated to 150° C., dynamically crystallized for 12 h. The stainless steel synthetic kettle was taken out from the oven and cooled. The solid product was centrifugal separated, washed to neutral using deionized water and dried at 100° C. in air to obtain a raw powder sample. 8.5 g of the raw powder sample was obtained (with mass loss of 16.4% after calcined at 600° C.) and the product yield was 39.5%. The sample was detected with XRD, indicating that the sample prepared was SAPO-34 molecular sieve. XRD data of sample were similar to Table 2, which showed that each corresponding peak had the same peak position, and the intensity of each corresponding peak was less than the sample obtained in Example 1, and the intensity of the strongest peak was about 70% of the sample obtained in Example 1. The elemental analysis of the surface composition and the bulk composition of the sample were detected with XPS and XRF, respectively, showing that the bulk composition was $Al_{0.50}P_{0.44}Si_{0.06}$ and the ratio of $Si_{surface}/Si_{bulk}$ was 2.0.

The sample (with the rhombohedral morphology and the crystal size from 1 μm to 3 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.08 and the atomic ratio of Si/Al near the surface area of the crystal was about 0.22.

COMPARATIVE EXAMPLE 2

16.4 g of phosphoric acid (85 wt %), 17.6 g of water and 10 g of pseudo-boehmite (72.5 wt %) were added into the synthetic kettle in sequence, stirred for 30 min to obtain a homogeneous mixture. 8.3 g of N,N,N',N'-tetramethyl ethylenediamine, 4.6 g of tetraethoxysilane, 1.4 g of HF solution (50%) and 11.2 g of deionized water were homogeneously mixed by stirring, and added to the homogeneous mixture obtained above. After stirring for 2 h under sealed condition, an initial gel mixture was obtained. The initial gel mixture was transferred into the stainless steel synthetic kettle, then heated to 190° C., dynamically crystallized for 12 h. The stainless steel synthetic kettle was taken out from the oven and cooled. The solid product was centrifugal separated, washed to neutral using deionized water and dried at 100° C. in air to obtain a raw powder sample. 16.1 g of the raw powder sample was obtained (with mass loss of 16.0% after calcined at 600° C.) and the product yield was 75.1%. The sample was detected with XRD, indicating that the sample prepared was SAPO-34 molecular sieve. XRD data of sample were similar to Table 2, which showed that each corresponding peak had the same peak position, and the intensity of each corresponding peak was less than the sample obtained in Example 1, and the intensity of the strongest peak was about 80% of the sample obtained in Example 1. The elemental analysis of the surface composition and the bulk composition of the samples were detected with XPS and XRF, respectively, showing that the bulk composition was $Al_{0.49}P_{0.41}Si_{0.10}$ and the ratio of $Si_{surface}/Si_{bulk}$ was 2.15.

The sample (with the rhombohedral morphology and the crystal size from 1 μm to 3 μm according to the SEM photo) was immobilized using epoxy resin and polished at a glazing machine. The composition analysis from the core to the shell was detected with SEM-EDX linear scanning of the crystal section near the crystal core. The result indicated that the atomic ratio of Si/Al near the core area of the crystal was about 0.15 and the atomic ratio of Si/Al near the surface area of the crystal was about 0.41.

COMPARATIVE EXAMPLE 3

16.4 g of phosphoric acid (85 wt %), 17.6 g of water and 10 g of pseudo-boehmite (72.5 wt %) were added into the synthetic kettle in sequence, stirred for 30 min to obtain a homogeneous mixture. 12.5 g of N,N,N',N'-tetramethyl ethylenediamine, 2.3 g of tetraethoxysilane and 11.2 g of deionized water were homogeneously mixed by stirring, and added to the homogeneous mixture obtained above. After stirring for 2 h under sealed condition, an initial gel mixture was obtained. The initial gel mixture was transferred into the stainless steel synthetic kettle, then heated to 190° C., dynamically crystallized for 12 h. The stainless steel synthetic kettle was taken out from the oven and cooled. The solid product was centrifugal separated, washed to neutral using deionized water and dried at 100° C. in air to obtain the sample which was not SAPO-34 molecular sieve according to the result of XRD analysis.

COMPARATIVE EXAMPLE 4 (Change of the Order of Ingredients Addation)

The amount of ingredients and the crystallization condition were the same as Example 1, except that the order of ingredients addation was changed. The process of ingredients addation was as follows: the aluminum source and the organic amine were mixed homogeneously by stirring, and then the phosphorus source was added, stirred for 20 min under sealed condition, and then the silicon source and deionized water were added, stirred vigorously for 30 min under sealed condition to obtain a homogenous gel mixture. The gel mixture was transferred into the stainless steel synthetic kettle, then heated to 190° C., dynamically crystallized for 12 h. After finishing the crystallization, the stainless steel synthetic kettle was taken out from the oven and cooled. The solid product was centrifugal separated, washed to neutral using deionized water and dried at 100° C. in air to obtain a raw powder sample. 18.5 g of the raw powder sample was obtained (with mass loss of 15.6% after calcined at 600° C.) and the product yield was 83.7%. The sample was detected with XRD, indicating that the sample prepared was SAPO-34 molecular sieve. XRD data of sample were similar to Table 2, which showed that each corresponding peak had the same peak position, and the intensity of each corresponding peak was less than the sample obtained in Example 1, and the intensity of the strongest peak was about 85% of the sample obtained in Example 1. The elemental analysis of the surface composition and the bulk composition of the sample were detected with XPS and XRF, respectively, showing that the ratio of $Si_{surface}/Si_{bulk}$ was 1.69.

COMPARATIVE EXAMPLE 5 (Change of the Order of Ingredients Addation)

The amount of ingredients and the crystallization condition were the same as Example 4, except that the order of ingredients addation was changed. The process of ingredients addation was as follows: the aluminum source and the organic amine were mixed homogeneously by stirring, and then the phosphorus source was added, stirred for 20 min under sealed condition, and then the silicon source and deionized water were added, stirred vigorously for 30 min under sealed condition to obtain a homogenous gel mixture. The gel mixture was transferred into the stainless steel synthetic kettle, then heated to 190° C., dynamically crystallized for 12 h. After finishing the crystallization, the stainless steel synthetic kettle was taken out from the oven and cooled. The solid product was centrifugal separated, washed to neutral using deionized water and dried at 100° C. in air to obtain a raw powder sample. 17.9 g of the raw powder sample was obtained (with mass loss of 15.1% after calcined at 600° C.) and the product yield was 81.6%. The sample was detected with XRD, indicating that the sample prepared was SAPO-34 molecular sieve. XRD data of sample were similar to Table 2, which showed that each corresponding peak had the same peak position and the slightly different peak intensity (≤±10%). The elemental analysis of the surface composition and the bulk composition of the sample were detected with XPS and XRF, respectively, showing that the ratio of $Si_{surface}/Si_{bulk}$ was 2.15.

EXAMPLE 24

The samples obtained in Example 18 and Comparative Example 1 were calcined at 600° C. for 4 hours in air, then pressed, crushed and sieved to 20-40 mesh. 1.0 g of this sample was weighted and loaded into a fixed bed reactor to carry out a methanol to olefins reaction evaluation. The sample was activated at 550° C. for 1 hour in nitrogen gas and reduced to 470° C. to perform a reaction. Methanol was carried by nitrogen gas with a flow rate of 40 ml/min and the Weight Hour Space Velocity of the methanol was 2.0 $h^{-1}$. The reaction products were analyzed by an on-line gas chromatograph (Varian3800, FID detector, capillary column was PoraPLOT Q-HT). The results were shown in Table 3.

TABLE 3

| | The reaction result of methanol to olefins on the sample | | | | | | | | |
|---|---|---|---|---|---|---|---|---|---|
| | Life | Selectivity (mass %) * | | | | | | | |
| Sample | (min) | $CH_4$ | $C_2H_4$ | $C_2H_6$ | $C_3H_6$ | $C_3H_8$ | $C_4^+$ | $C_5^+$ | $C_2H_4 + C_3H_6$ |
| Example 18 | 200 | 1.8 | 44.9 | 0.8 | 40.0 | 1.4 | 9.1 | 2.0 | 84.9 |
| Comparative Example 1 | 120 | 2.3 | 43.8 | 1.0 | 38.0 | 2.0 | 10.8 | 2.1 | 81.8 |

* The highest (ethylene + propylene) selectivity when methanol conversion was 100%.

slightly different peak intensity (<±10%). The elemental analysis of the surface composition and the bulk composition of the sample were detected with XPS and XRF, respectively, showing that the ratio of $Si_{surface}/Si_{bulk}$ was 1.79.

COMPARATIVE EXAMPLE 6 (Change of the Order of Ingredients Addation)

The amount of ingredients and the crystallization condition were the same as Example 4, except that the order of ingredients addation was changed, and a small quantity of ethanol was added into the synthesis system, and an ageing process was used. The process of ingredients addation was as follows: the aluminum source and the organic amine were mixed homogeneously by stirring, and then the silicon source was added, stirred for 20 min under sealed condition, and then the phosphorus source, 1.0 g of ethanol and deionized water were added, stirred vigorously for 30 min under sealed condition, and then the mixture was aged by being stirred for 12 h at 40° C. to obtain a homogenous gel mixture. The gel mixture was transferred into the stainless steel synthetic kettle, then heated to 190° C., dynamically crystallized for 12 h. After finishing the crystallization, the stainless steel synthetic kettle was taken out from the oven and cooled. The solid product was centrifugal separated, washed to neutral using deionized water and dried at 100° C. in air to obtain a raw powder sample. 16.9 g of the raw powder sample was obtained (with mass loss of 14.7% after calcined at 600° C.) and the product yield was 77.4%. The sample was detected with XRD, indicating that the sample prepared was SAPO-34 molecular sieve. XRD data of sample were similar to Table 2, which showed that each corresponding peak had the same peak position and the

EXAMPLE 25

The samples obtained in Example 1 and Comparative Example 2 were calcined at 600° C. for 4 hours in air, then pressed, crushed and sieved to 20-40 mesh. 1.0 g of this sample was weighted and loaded into a fixed bed reactor to carry out ethanol dehydration reaction evaluation. The sample was activated at 550° C. for 1 hour in nitrogen gas and reduced to 260° C. to perform a reaction. Ethanol was carried by nitrogen gas with a flow rate of 40 ml/min and the Weight Hour Space Velocity of the ethanol was 2.0 $h^{-1}$. The reaction products were analyzed by an on-line gas chromatograph (Varian3800, FID detector, capillary column was PoraPLOT Q-HT). The results indicated that on the sample obtained in Example 1, ethanol conversion was 95% and selectivity for ethylene was 99.5%. On the sample obtained in Comparative Example 2, ethanol conversion was 70% and selectivity for ethylene was 90%, and the product containing the hydrocarbon by-products, such as methane, and the like.

EXAMPLE 26

The sample obtained in Example 1 was used for propylene adsorbent. The adsorption isotherm of the sample was detected by ASAP2020 of US Micromeritics. The adsorbed gases were propylene (99.99%), propane (99.99%). In order to avoid the influence of physical absorb water in molecular sieve, the sample was calcined at 600° C. for 4 hours in air before the adsorption isotherm detection. Then the sample was heated to 350° C. at the rate of 1° C./min in an extremely low vacuum ($5\times10^{-3}$ mmHg) and kept for 8 hours. The adsorbent temperature was 298K and controlled by thermostatic water bath (accuracy: ±0.05° C.). The result indicated that the adsorption capacities of propylene and propane were 1.95 and 1.0 mmol/g (at 101 kPa) respectively. The adsorption selectivity was propylene/propane=1.95.

The sample after the adsorption was vacuumed at room temperature for 30 min by ASAP2020, and then detected again for the adsorption isotherm. The adsorption capacities of propylene and propane were 2.00 and 1.05 mmol/g (at 101 kPa) respectively. The result indicated that the sample had good regeneration performance which can be regenerated under very mild conditions.

The invention claimed is:

1. A SAPO-34 molecular sieve with a chemical composition in the anhydrous state expressed as:

$$mSDA \cdot (Si_xAl_yP_z)O_2;$$

wherein,

SDA represents the template agent existing in micropores of the molecular sieve;

SDA is organic amine with the structural formula as $(CH_3)_2NRN(CH_3)_2$, wherein R is saturated straight-chain or branch-chain alkylene group with the number of carbon atoms at a range from 2 to 5;

m is the molar number of the template agent per one mole of $(Si_xAl_yP_z)O_2$, and m is from 0.08 to 0.3;

x, y, z respectively represents the molar number of Si, Al, P, and x is from 0.01 to 0.60, and y is from 0.2 to 0.60, and z is from 0.2 to 0.60, and x +y +z =1; and wherein the molecular sieve is a crystal, there is a slight Si enrichment phenomenon on a crystal surface molecular sieve crystal, and the ratio of surface Si content to bulk Si content of the crystal ranges from 1.50 to 1.01; wherein the Si content is calculated by the molar ratio of Si/(Si+Al+P).

2. The SAPO-34 molecular sieve according to claim 1, wherein the ratio of the surface Si content to the bulk Si content of the crystal ranges from 1.42 to 1.02.

3. The SAPO-34 molecular sieve according to claim 1, wherein the template agent SDA is one or more selected from N,N,N',N'-tetramethyl ethylenediamine, N,N,N',N'-tetramethyl -1,3-diaminopropane, N,N,N',N'-tetramethyl-1,4-butanediamine, N,N,N',N'-tetramethyl-1,5-pentane diamine, N,N,N',N'-tetramethyl-1,2-diaminopropane, N,N,N',N'-tetramethyl-1,3-butanediamine, and N,N,N',N'-tetramethyl-1, 4-pentane diamine.

4. The SAPO-34 molecular sieve according to claim 1, wherein the surface Si content to the bulk Si content of the crystal ratio ranges from 1.30 to 1.03.

5. A method for preparing the SAPO-34 molecular sieve according to claim 1, including the steps as follows:
(a) mixing a silicon source, an aluminum source, a phosphorus source, deionized water and SDA thereby obtaining an initial gel mixture with following molar ratio:
$SiO_2/Al_2O_3$ is from 0.01 to 1;
$P_2O_5/Al_2O_3$ is from 0.5 to 1.5;
$H_2O/Al_2O_3$ is from 1 to 19;
$SDA/Al_2O_3$ is from 5 to 30; and
$SDA/H_2O$ is from 0.27 to 30;
wherein, SDA is organic amine with the structural formula as $(CH_3)_2NRN(CH_3)_2$, wherein R is saturated straight-chain or branch-chain alkylene group with the number of carbon atoms at a range from 2 to 5;
(b) transferring the initial gel mixture into a synthetic kettle, then sealing and heating to crystallization temperature range from 170° C. to 220° C., crystalizing for a crystallization time range from 0.5 h to 48 h under autogenous pressure; and
(c) after finishing the crystallization, centrifuging and separating the solid product, followed by washing to neutral using deionized water and drying to obtain the SAPO-34 molecular sieve;
wherein the initial gel mixture is mixed with the following order of ingredient addition is: firstly, mixing homogeneously the aluminum source and the organic amine SDA by stirring to obtain a Mixture A; separately and continuously stirring a mixture of the silicon source, the phosphorus source and deionized water, and adding the homogeneously the Mixture A thereto and stirring to obtain the initial gel mixture.

6. The method according to claim 5, wherein in the initial gel mixture, the silicon source is one or more selected from silica sol, active silica, orthosilicate esters and metakaolin; the aluminum source is one or more selected from aluminum salts, activated alumina, aluminum alkoxide and metakaolin; and the phosphorus source is one or more selected from phosphoric acid, diammonium hydrogen phosphate, ammonium dihydrogen phosphate, organophosphorous compounds and phosphorus oxides.

7. The method according to claim 5, wherein in the initial gel mixture, the molar ratio of organic amine SDA to water $SDA/H_2O$ is from 0.5 to 30 .

8. The method according to claim 5, wherein in the initial gel mixture, the molar ratio of organic amine SDA to $Al_2O_3$ $SDA/Al_2O_3$ is from 7.0 to 30 .

9. The method according to claim 5, wherein the organic amine SDA is selected from N,N,N',N'-tetramethyl ethylenediamine, N,N,N',N'-tetramethyl-1,3-diaminopropane, N,N,N',N'-tetramethyl-1,4-butanediamine, N,N,N',N'-tetramethyl-1,5-pentane diamine, N,N,N',N'-tetramethyl-1,2-diaminopropane, N,N,N',N'-tetramethyl-1,3-butanediamine, and N,N,N',N'-tetramethyl-1,4-pentane diamine.

10. The method according to claim 5, wherein the crystallization temperature ranges from 180° C. to 210° C. and the crystallization time ranges from 1 h to 24 h.

11. The method according to claim 5, wherein in the initial gel mixture the molar ratio of organic amine SDA to water $SDA/H_2O$ is from 1.0 to 30 .

12. The method according to claim 5, wherein the crystallization temperature ranges from 190° C. to 210° C.

13. The method according to claim 5, the crystallization time ranges from 1 h to 12 h.

14. A process for producing ethylene from ethanol using a catalyst, wherein the catalyst is obtained by calcining at least one of the SAPO-34 molecular sieves according to claim 1, at a temperature from 400 to 700° C. in air.

15. A process for producing olefins from oxygenates using a catalyst, wherein the catalyst is obtained by calcining at least one of the SAPO-34 molecular sieves according to claim 1, at a temperature from 400 to 700° C. in air.

* * * * *